(12) United States Patent
Duffy et al.

(10) Patent No.: US 10,261,010 B2
(45) Date of Patent: Apr. 16, 2019

(54) METHOD FOR SPECTROPHOTOMETRICALLY DETERMINING A BLOOD OXYGEN PARAMETER

(71) Applicant: CAS Medical Systems, Inc., Branford, CT (US)

(72) Inventors: Karen Duffy, Orange, CT (US); Matthew Dalene, Clinton, CT (US); John Gamelin, Avon, CT (US); Paul Benni, Acton, MA (US)

(73) Assignee: CAS Medical Systems, Inc., Branford, CT (US)

( * ) Notice: Subject to any disclaimer, the term of this patent is extended or adjusted under 35 U.S.C. 154(b) by 698 days.

(21) Appl. No.: 14/651,160

(22) PCT Filed: Dec. 10, 2013

(86) PCT No.: PCT/US2013/074127
§ 371 (c)(1),
(2) Date: Jun. 10, 2015

(87) PCT Pub. No.: WO2014/093342
PCT Pub. Date: Jun. 19, 2014

(65) Prior Publication Data
US 2015/0308946 A1 Oct. 29, 2015

Related U.S. Application Data

(60) Provisional application No. 61/735,354, filed on Dec. 10, 2012, provisional application No. 61/791,146, filed on Mar. 15, 2013.

(51) Int. Cl.
*A61B 5/1455* (2006.01)
*G01N 21/35* (2014.01)
(Continued)

(52) U.S. Cl.
CPC ......... *G01N 21/35* (2013.01); *A61B 5/14552* (2013.01); *A61B 5/14553* (2013.01);
(Continued)

(58) Field of Classification Search
None
See application file for complete search history.

(56) References Cited

U.S. PATENT DOCUMENTS 5,817,008 A 10/1998 Rafert et al.
6,456,862 B2 9/2002 Benni
(Continued)

FOREIGN PATENT DOCUMENTS

WO WO2006110488 A2 10/2006

OTHER PUBLICATIONS

Japanese office action for JP2015-547470 dated May 31, 2016.
EP search report for EP13861614.9 dated Jul. 12, 2016.

*Primary Examiner* — Eric F Winakur
*Assistant Examiner* — Marjan Fardanesh
(74) *Attorney, Agent, or Firm* — O'Shea Getz P.C.

(57) ABSTRACT

According to an aspect of the present invention, a near infrared spectroscopy (NIRS) sensor assembly, system, and method for measuring a characteristic of a biological tissue is provided. The NIRS sensor assembly includes a light source, at least one light detector, and a subject contact layer. The light source is operable to emit light at one or more predetermined wavelengths. The light detector has an active area for detecting light emitted by the light source and passed through the biological tissue. The detector is operable to produce signals representative of the detected light. The subject contact layer is disposed to cover one or both of the light detector and the light source. The subject contact layer has at least one optically transmissive portion.

10 Claims, 9 Drawing Sheets

(51) Int. Cl.
*A61B 5/00* (2006.01)
*G01N 33/49* (2006.01)

(52) U.S. Cl.
CPC ....... *A61B 5/6832* (2013.01); *G01N 33/4925* (2013.01); *A61B 2562/0238* (2013.01); *A61B 2562/146* (2013.01); *A61B 2562/164* (2013.01)

(56) References Cited

U.S. PATENT DOCUMENTS

| | | |
|---|---|---|
| 7,047,054 B2 | 5/2006 | Benni |
| 7,072,701 B2 | 7/2006 | Chen et al. |
| 7,190,986 B1 | 3/2007 | Hannula et al. |
| 7,313,427 B2 | 12/2007 | Benni |
| 8,396,526 B2 | 3/2013 | Benni |
| 2002/0016536 A1 | 2/2002 | Benni |
| 2006/0224055 A1 | 10/2006 | Kermani et al. |
| 2010/0049018 A1 | 2/2010 | Duffy et al. |
| 2012/0065485 A1 | 3/2012 | Benni et al. |
| 2013/0012822 A1 | 1/2013 | Kosturko et al. |
| 2014/0051956 A1 | 2/2014 | Dalene et al. |
| 2014/0121481 A1 | 5/2014 | Abrams et al. |
| 2014/0171761 A1 | 6/2014 | Dalene et al. |

METHOD FOR SPECTROPHOTOMETRICALLY DETERMINING A BLOOD OXYGEN PARAMETER

This application claims priority to PCT Patent Appln. No. PCT/US2013/074127 filed Dec. 10, 2013, which claims priority to U.S. Patent Appln. No. 61/735,354 filed Dec. 10, 2012 and U.S. Patent Appln. No. 61/791,146 filed Mar. 15, 2013.

BACKGROUND

1. Technical Field

Aspects of the present invention generally relate to non-invasive spectrophotometric medical devices, and more particularly relate to non-invasive medical devices that include a sensor with a subject contact layer.

2. Background Information

Non-invasive medical devices (e.g., near-infrared spectroscopy (NIRS) sensor assemblies, pulse oximetry sensor assemblies, etc.) often include one or more light emitting components (e.g., light emitting diodes (LEDs), laser diodes, etc.) that emit light signals (e.g., visible light signals, near-infrared light signals, etc.) and one or more light detecting components (e.g., photodiodes, charge-coupled devices, etc.) that detect light signals emitted by the light emitting components, for example, after such light signals pass through a biological tissue. A problem common to non-invasive medical devices is discomfort and/or irritation experienced by a subject when a non-invasive medical device is in contact with the subject over a period of time. Aspects of the present invention are directed to this and other problems.

SUMMARY OF THE INVENTION

According to an aspect of the present invention, a near-infrared spectroscopy (NIRS) sensor assembly for measuring a characteristic of a biological tissue is provided. The NIRS sensor assembly includes a light source, at least one light detector, and a subject contact layer. The light source is operable to emit light at one or more predetermined wavelengths. The light detector has an active area for detecting light emitted by the light source and passed through the biological tissue. The detector is operable to produce signals representative of the detected light. The subject contact layer is disposed to cover one or both of the light detector and the light source. The subject contact layer has at least one optically transmissive portion.

According to another aspect of the present invention, a near-infrared spectroscopy (NIRS) system for measuring a characteristic of a biological tissue is provided. The system includes at least one sensor assembly as described herein, and a processor. The processor is adapted to use the signals produced by the detector to determine the characteristic of the tissue. The processor is also adapted to account for the optical transmissivity of the subject contact layer when determining the characteristic of the tissue.

According to another aspect of the present invention, a method for determining a blood oxygen parameter of a subject tissue is provided. The method comprises the steps of: a) providing a near-infrared spectroscopy (NIRS) system as described herein; b) interrogating the subject tissue with light emitted from the sensor assembly; c) detecting light emitted by the light source, which light has passed through the biological tissue and has passed through a material of the subject contact layer, and producing signals representative of the detected light; and d) determining the blood oxygen parameter of the subject tissue using the processor and the signals representative of the detected light, which determination includes accounting for the optical transmissivity of the subject contact layer.

Embodiments of any of the above described aspects of the present invention may also include one or more of the following elements. For example, the NIRS sensor assembly may include a pad having at least one light detector aperture aligned with the light detector, and at least one light source aperture aligned with the at least one light detector. In this embodiment the subject contact layer may be disposed to cover both the light source and the at least one detector, and the at least one optically transmissive portion of the subject contact layer may include portions aligned with the light source and the at least one detector. As another example, the subject contact layer may be disposed within the light detector aperture. As another example, the subject contact layer may include an optically non-transmissive portion that is not aligned with the active area of the light detector. As another example, the subject contact layer may be made from one or more materials, including: a silicone foam, a polyethylene foam, a polyurethane foam, a polyvinyl chloride foam, a tricot fabric, a knit fabric, a loose weave fabric, a spunlace fabric, a microporous fabric, an elastic fabric, a hydrogel adhesive, a hydrocolloid adhesive, or an encapsulated gel. As another example, the sensor assembly may include a layer of electromagnetic (EMI) shielding disposed between the light detector and the subject contact layer. As another example, the sensor assembly may include a layer of EMI shielding incorporated into the subject contact layer. As another example, the sensor assembly may include a layer of electrically insulating material disposed between the light detector and the subject contact layer. As another example, the sensor assembly may include a layer of electrically insulating material is incorporated into the subject contact layer. As another example, the subject contact layer may have one or both of uniform optical attenuation characteristics and uniform light scattering characteristics.

The above described aspects of the present invention and embodiments may be used individually or in combination with one another, and the present invention is not limited to any particular configuration. These and other aspects, embodiments, features, and advantages of the present invention will become apparent in light of the detailed description of the invention provided below, and as illustrated in the accompanying drawings.

DETAILED DESCRIPTION

The present disclosure describes embodiments of a NIRS sensor assembly; however, aspects of the present invention may be applied to other types of non-invasive medical devices, including, for example, pulse oximetry sensor assemblies.

The NIRS sensor assembly described herein can be used in connection with various types of NIRS systems. In the embodiment illustrated in FIG. 1, the NIRS sensor assembly 10 is used in connection with a NIRS system 12 that includes a base unit 14. The base unit 14 includes a display 16, operator controls 18, and a processor 20 for providing signals to and/or receiving signals from the NIRS sensor assembly 10. The processor 20 includes one or more central processing units (CPUs) adapted (e.g., programmed) to selectively perform the functions necessary to perform the functions described herein. For example, the processor 20 is adapted to operate the NIRS sensor assembly 10 to emit light signals from the light source 22, to receive sensor signals from the light detectors 24, 26, and to determine a characteristic of the tissue (e.g., blood oxygen saturation value) using the sensor signals. The processor 20 is further adapted for use with a NIRS sensor assembly 10 calibrated in the manner described below. U.S. Pat. Nos. 7,072,701 and 8,396,526, both of which are hereby incorporated by reference in their entirety, describe examples of NIRS oximetry systems having processors adapted to determine blood oxygen saturation values. The methodologies described in these patents are examples of methodologies that can be adapted pursuant to aspects of the present invention as will be described below. The present invention has broader applicability that these specific methodologies, however, and is therefore not limited to the methodologies described in these patents. The functionality of processor 20 may be implemented using hardware, software, firmware, or a combination thereof. A person skilled in the art would be able to adapt (e.g., program) the processor 20 to perform the functionality described herein without undue experimentation.

Referring to FIGS. 2-7, the NIRS sensor assembly 10 includes one or more light sources 22, one or more light detectors 24, 26, a circuit 28, a connector 30, a pad 32, a subject contact layer 34, and a cover 36. In some embodiments, including the embodiment illustrated in FIGS. 2-7, the NIRS sensor assembly 10 may additionally include a cover 36. The NIRS sensor assembly 10, and/or features of the NIRS sensor assembly 10, may be described as having a length extending along an x-axis, a width extending along a y-axis, and/or a height extending along a z-axis. The drawings illustrate the respective axes.

The light source 22 includes one or more light emitting components (e.g., light emitting diodes ("LEDs"), laser diodes, etc.) that are selectively operable to emit light at one or more predetermined wavelengths through an active region. The light emitted by the light source 22 includes light in the infrared range (i.e., in the wavelength range of about seven hundred nanometers (700 nm) to about one thousand nanometers (1,000 nm)) and/or the visible range (i.e., in the wavelength range of about three hundred ninety nanometers (390 nm) to about seven hundred fifty nanometers (750 nm)). The light source 22 may be mounted on the circuit 28 for electrical connection to the base unit 14 (see FIG. 1), as will be described below.

The light detectors 24, 26 each include one or more light detecting components (e.g., photodiodes, charge-coupled devices, etc.) that are selectively operable to detect light signals emitted by the light source 22 through an active region and produce signals representative of such detected light, which signals may be sent to the processor 20. The light detectors 24, 26 may detect the light, for example, after it passes through a biological tissue (e.g., brain tissue) of a subject. The light detectors 24, 26 may be mounted on the circuit 28 for electrical connection to the base unit 14 (see FIG. 1), as will be described below. As will also be described below, the NIRS sensor assembly 10 may be configured so that one or more of the light detectors 24, 26 can be used in measuring the optical transmissivity of the subject contact layer 34, and/or the optical transmissivity of one or more other components of the NIRS sensor assembly 10 that light signals are intended to pass through before being detected by the light detectors 24, 26.

The light source 22 and the light detectors 24, 26 can assume various relative positions on the NIRS sensor assembly 10. International Patent Application No. PCT/US12/24889, which is hereby incorporated by reference in its entirety, discloses several examples of acceptable relative positions. The relative position of the light source 22 and the light detectors 24, 26 may preferably be selected so that: (1) the light source 22 and the light detectors 24, 26 are at least substantially linearly aligned along a lengthwise-extending axis 38 (see FIG. 2); and (2) the separation distances between the light source 22 and each of the light detectors 24, 26 are not the same.

The circuit 28 electrically connects the light source 22 and the light detectors 24, 26 to the connector 30. The connector 30, in turn, provides the structure that allows the NIRS sensor assembly 10 to be electrically connected to the base unit 14 (see FIG. 1). The NIRS sensor assembly 10 can include various types of circuits 28. In the embodiments illustrated in FIGS. 1-7, the circuit 28 is a flexible circuit that is similar to ones described in U.S. Patent Application No. 61/735,318, which is hereby incorporated by reference in its entirety.

Figure 1:
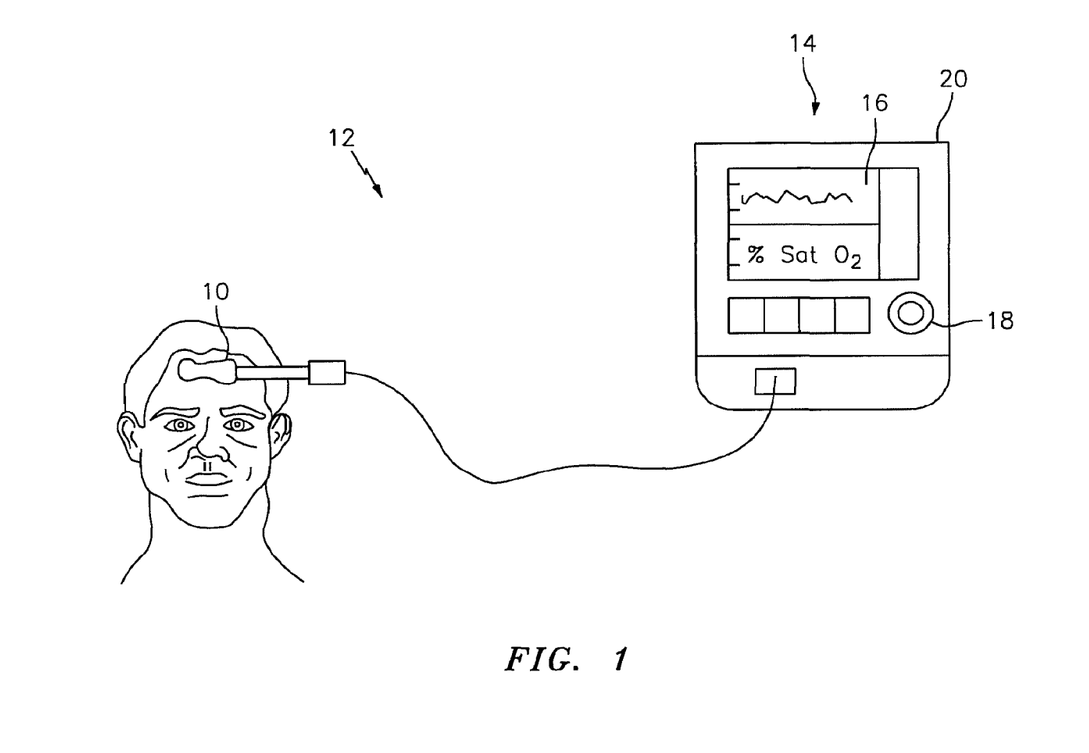
FIG. 1 is a diagrammatic view of a NIRS sensor assembly used in connection with a NIRS system.
Figure 2:
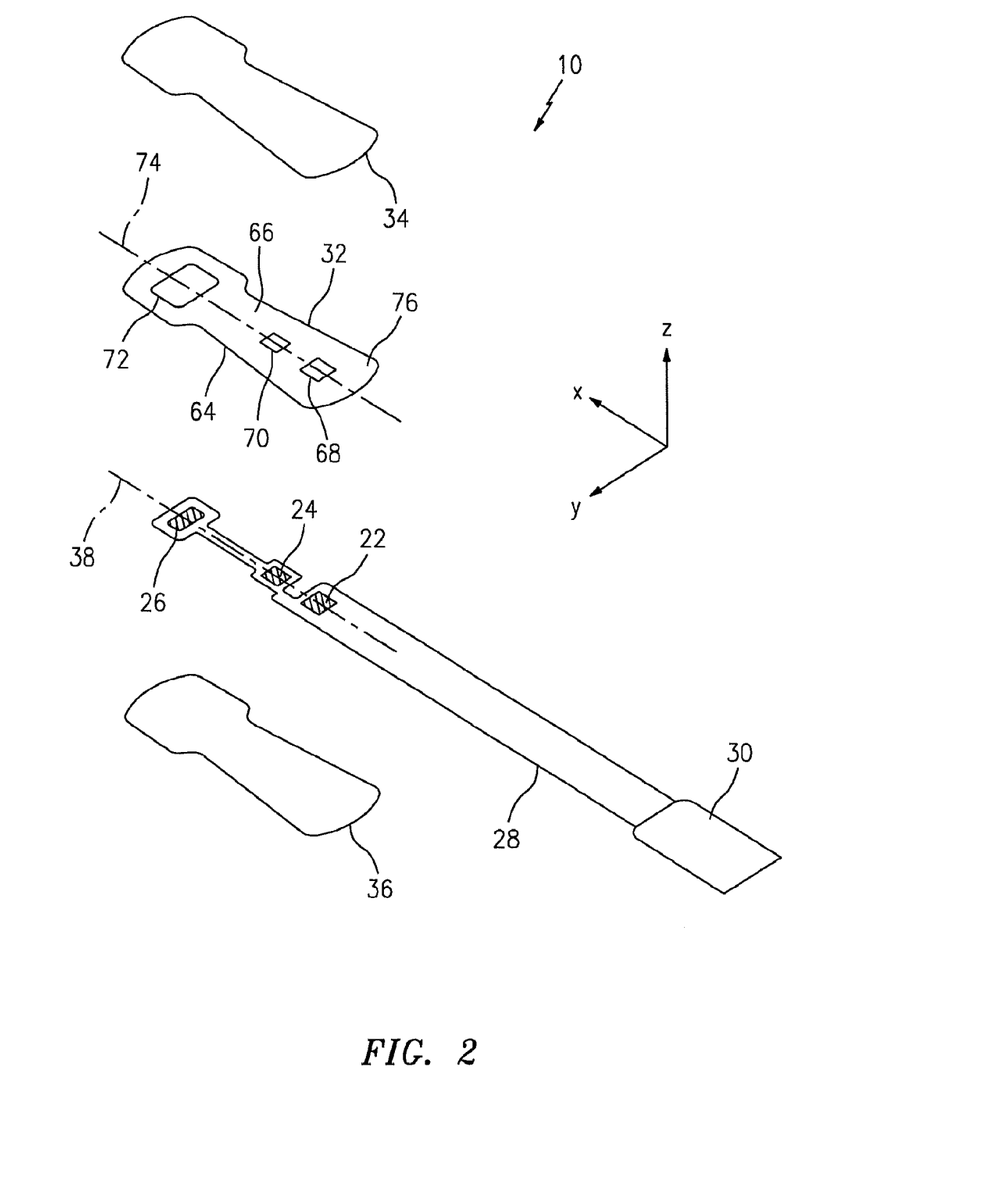
FIG. 2 is an exploded plan view of a NIRS sensor assembly of FIG. 1.
Figure 3:
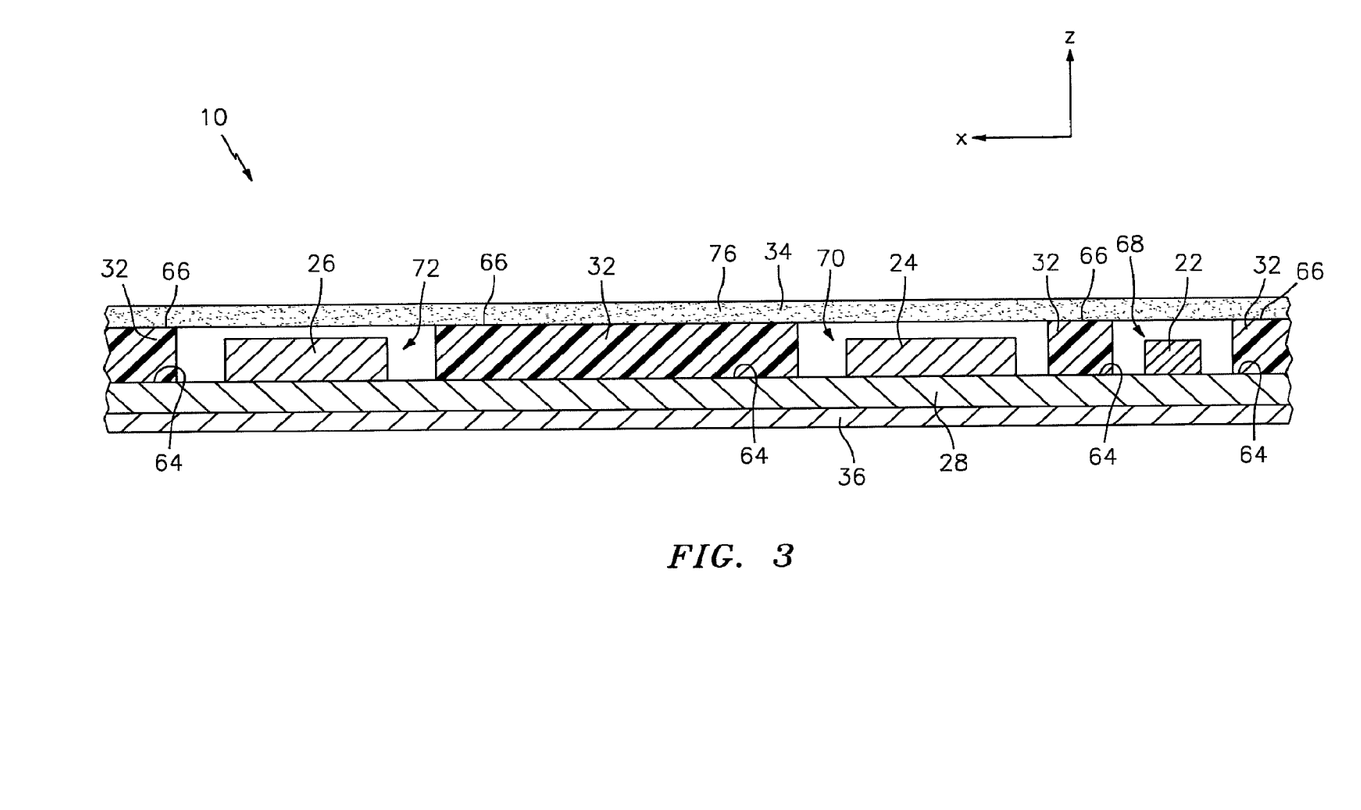
FIG. 3 is a sectional elevation view of the NIRS sensor assembly of FIG. 1.
Figure 4:
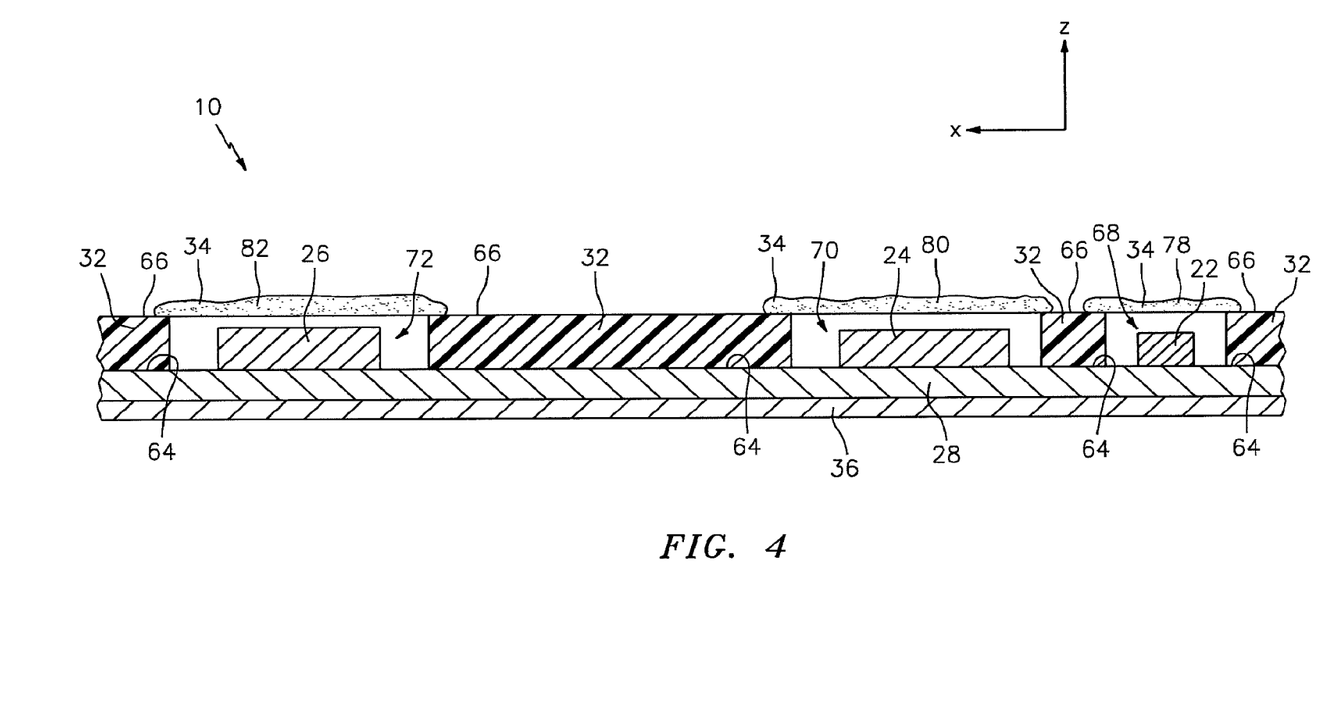
FIG. 4 is a sectional elevation view of another NIRS sensor assembly.
Figure 5:
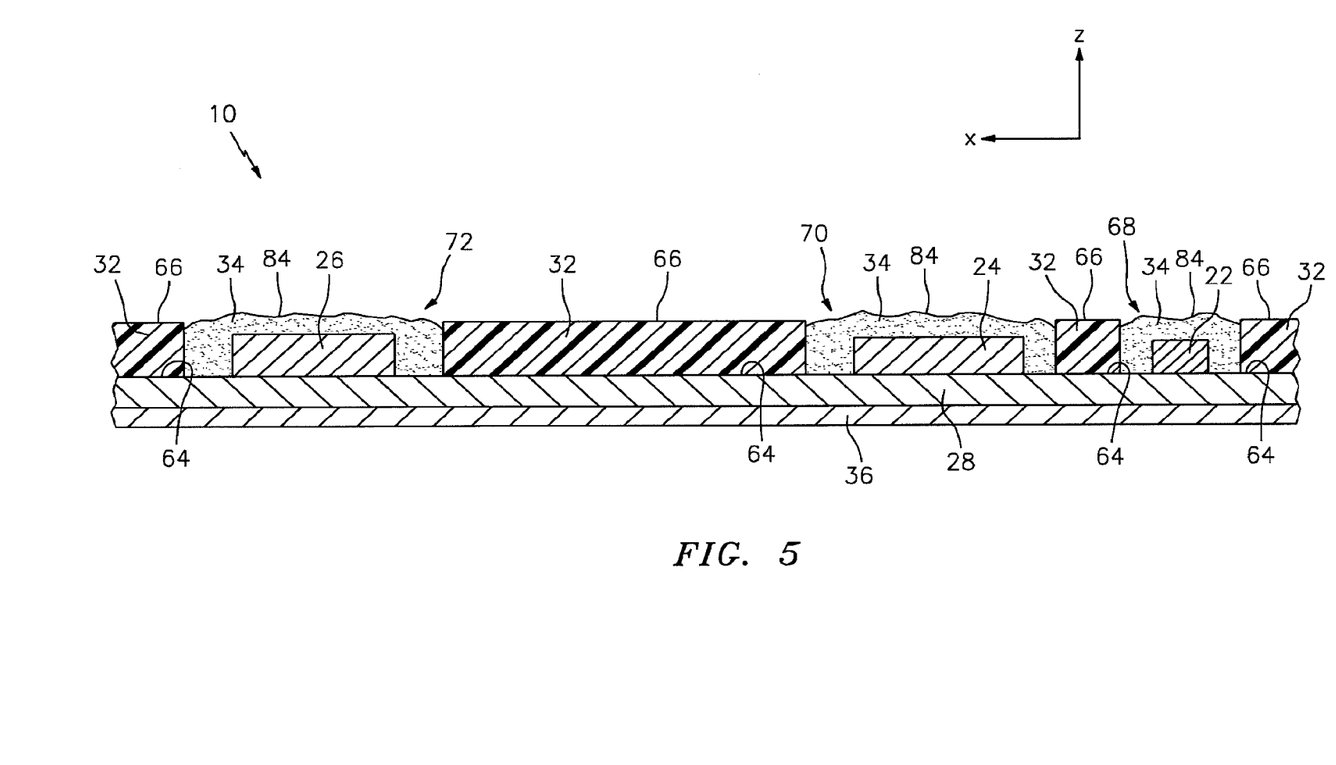
FIG. 5 is a sectional elevation view of another NIRS sensor assembly.
Figure 6:
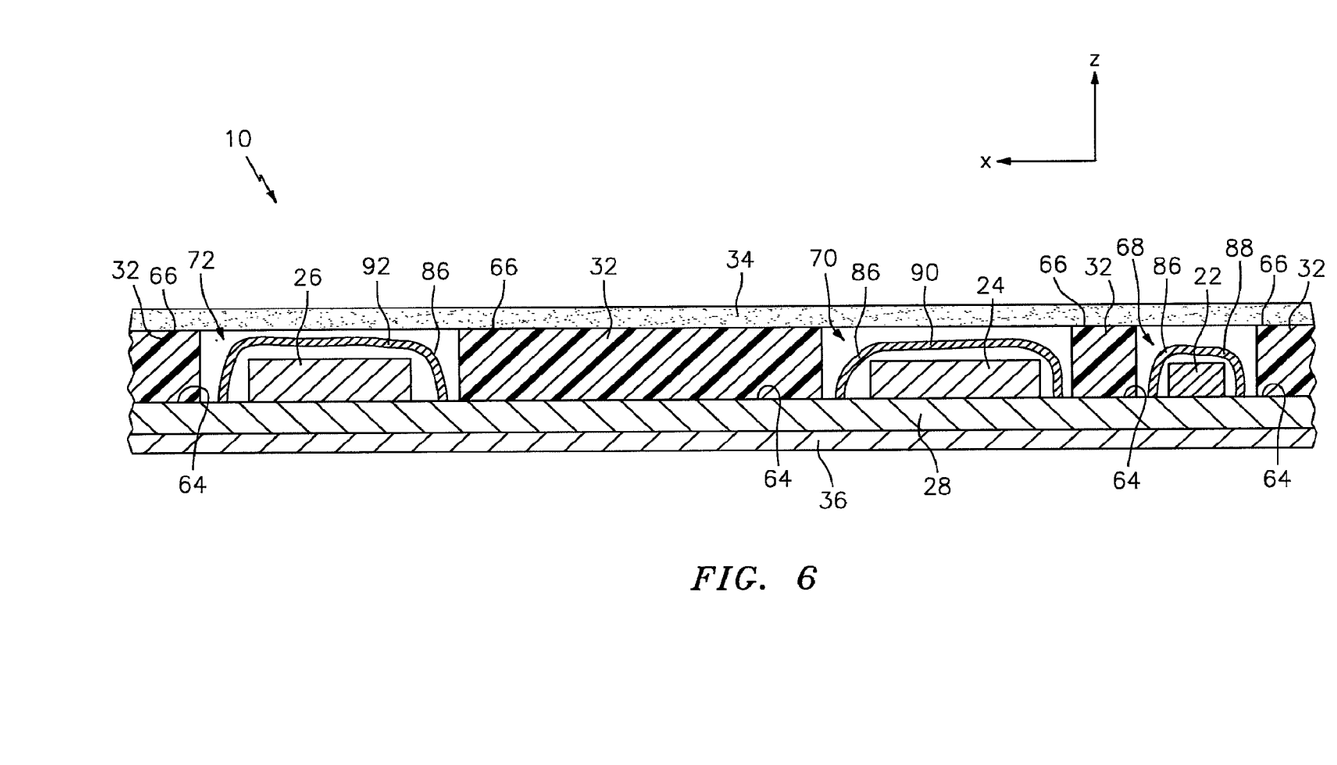
FIG. 6 is a sectional elevation view of another NIRS sensor assembly.
Figure 7:
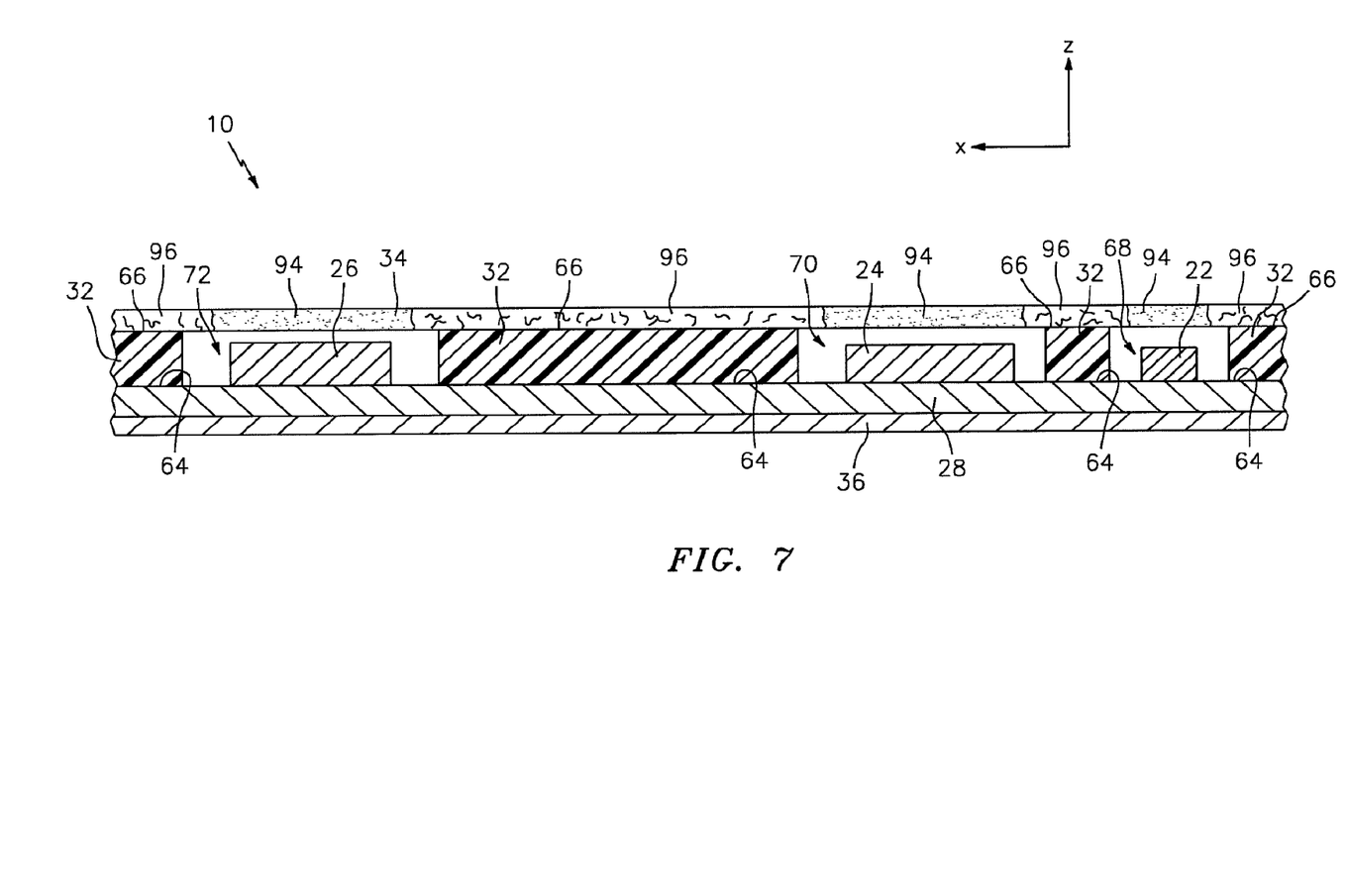
FIG. 7 is a sectional view of another NIRS sensor assembly.

Referring to FIGS. 1 and 2, the connector 30 is configured to provide electrical communication, directly or indirectly, between the NIRS sensor assembly 10 and the base unit 14. The NIRS sensor assembly 10 can include various types of connectors 30. In some embodiments, the connector 30 may be the same as or similar to the connectors disclosed in International Patent Application No. PCT/US12/24889, and in U.S. Provisional Patent Application No. 61/717,401, both of which are hereby incorporated by reference in their entirety. In some embodiments, the present NIRS sensor assembly 10 may not include a connector 30.

Referring to FIGS. 2-7, the pad 32 is disposed relative to the circuit 28. The pad 32 includes a bottom surface 64 and an opposing top surface 66; at least one light source aperture 68 that extends in a heightwise direction between the bottom surface 64 and the top surface 66; and one or more light detector apertures 70, 72 that extend in a heightwise direction between the bottom surface 64 and the top surface 66.

The pad 32 may be optically non-transmissive. The term "optically non-transmissive" is used herein relative to the pad 32 to describe that light signals emitted by the light source 22 during normal operation of the NIRS sensor assembly 10 may be blocked or otherwise prevented from passing through the pad 32 to an extent that any light signals that do pass through and exit the pad 32 have a luminescent intensity that is inadequate for a NIRS measurement.

The pad 32 may be positioned on the NIRS sensor assembly 10 so that the light source 22 is at least partially disposed within the light source aperture 68, and so that the light detectors 24, 26 are at least partially disposed within the respective light detector apertures 70, 72. The bottom surface 64 of the pad 32 may be attached (e.g., using an adhesive), directly or indirectly, to the circuit 28. In the embodiments illustrated in FIGS. 2-7, the bottom surface 64 of the pad 32 is attached directly to the circuit 28. The pad 32 can have various geometries. In the embodiment illustrated in FIG. 2, the geometry of the pad 32 is such that the light source aperture 68 and the light detector apertures 70, 72 are linearly aligned along a lengthwise-extending axis 74.

The pad 32 can be made from various materials or combinations of materials. An example of an acceptable material for the pad 32 is one that is soft and pliable, and suitable for a patient environment. A specific example of an acceptable pad 32 material is Poron® cellular urethane foam, a product of Rogers Corporation of Woodstock, Conn., U.S.A.

Referring to FIGS. 2-7, the subject contact layer 34 is disposed relative to the pad 32 to cover exposed portions of the light detectors 24, 26 and, in some embodiments, exposed portions of the light source 22. The subject contact layer 34 includes a bottom surface 33 and an opposing top surface 35. In some embodiments, the subject contact layer 34 may be in the form of a sheet that is connected (e.g., using adhesives), either directly or indirectly, to the circuit 28. In the embodiments illustrated in FIGS. 2-6, for example, the subject contact layer 34 is in the form of a sheet, and the bottom surface 33 of the subject contact layer 34 is attached directly to the top surface 66 of the pad 32. In other embodiments, the subject contact layer 34 may be in the form of a coating that is disposed at least partially within one or more of the apertures 68, 70, 72 within the pad 32. In the embodiment illustrated in FIG. 7, for example, the subject contact layer 34 is in the form of a coating that is disposed within each of the light source aperture 68 and the light detector apertures 70, 72 of the pad 32.

One or more portions, or all portions, of the subject contact layer 34 are optically transmissive. In some embodiments, one or more portions of the subject contact layer 34 may be optically non-transmissive. The term "optically transmissive" is used herein relative to portions of the subject contact layer 34 to describe that light signals emitted by the light source 22 during normal operation of the NIRS sensor assembly 10 may pass through and exit the portions with a luminescent intensity that is adequate for a NIRS measurement. The term "optically non-transmissive" is used herein relative to portions of the subject contact layer 34 to describe that light signals emitted by the light source 22 during normal operation of the NIRS sensor assembly 10 are blocked or otherwise prevented from passing through the portions to an extent that any light signals that do pass through and exit the portions have a luminescent intensity that is inadequate for a NIRS measurement. The terms "optically transmissive" and "optically non-transmissive" are not used herein to describe visual transparency to the human eye, or visual non-transparency to the human eye. The term "optical transparency" is used herein relative to the subject contact layer 34 to describe that light at wavelengths and intensity transmitted by the light source and collected by the light detectors, can transmit through the subject contact layer 34 and into the subject tissue, or can transmit through the subject contact layer 34 from the subject tissue, and be detected by the light detectors. The optical transmissivity of the subject contact layer 34 may depend on one or more characteristics of the subject contact layer 34, including, for example, a dimension of the subject contact layer 34, and/or a material of the subject contact layer 34. In some embodiments, for example, the optical transmissivity may depend on a distance that extends in a heightwise direction between the bottom surface 33 and the top surface 35 of the subject contact layer 34.

The subject contact layer 34 is positioned on the NIRS sensor assembly 10 so that the one or more portions of the subject contact layer 34 that are optically transmissive are aligned with the active region of the light source 22 and the active regions of each of the light detectors 24, 26. In the embodiment illustrated in FIG. 4, for example, the subject contact layer 34 includes optically transmissive portions 94 aligned with active regions of the light source 22 and the light detectors 24, 26, and optically non-transmissive portions 96 elsewhere. The subject contact layer 34 is positioned on the NIRS sensor assembly 10 so that the top surface 33 of the subject contact layer 34 may contact the subject tissue being sensed during operation of the NIRS sensor assembly 10. In some embodiments, the subject contact layer has a predetermined thickness and has known and/or uniform optical attenuation and scattering characteristics.

The subject contact layer 34 may include one continuous section, or a plurality of discrete sections. In the embodiments illustrated in FIGS. 2-4 and 6, the subject contact layer 34 includes one continuous section. In the embodiment illustrated in FIGS. 5 and 7, however, the subject contact layer 34 includes three discrete sections 37, 39, 41. The subject contact layer 34 can have various geometries. The geometry of the subject contact layer 34 may be such that the subject contact layer 34 is operable to cover the entire top surface 66 of the pad 32, or the geometry may be such that the subject contact layer 34 is operable to cover only one or more portions of the top surface 66 of the pad 32. In the embodiment shown in FIGS. 3, 4, and 6, for example, the subject contact layer 34 is attached to and covers the entire top surface 66 of the pad 32, including the light source aperture 68 and the light detector apertures 70, 72. In the embodiment shown in FIG. 5, in contrast, the three discrete sections 37, 39, 41 of the subject contact layer 34 each cover a portion of the top surface 66 of the pad 32, leaving other portions of the top surface 66 exposed. In the embodiment shown in FIG. 5, the three discrete sections 37, 39, 41 of the subject contact layer 34 cover the light source aperture 68, the first light detector aperture 70, and the second light detector aperture 72, respectively.

The subject contact layer 34 can be made from various materials or combinations of materials. The subject contact layer 34 may include one or more foam materials, one or more woven fabric materials, one or more non-woven fabric materials, one or more gel materials, or a combination thereof. Examples of acceptable foam materials include: silicone foams; polyethylene foams; polyurethane foams; and polyvinyl chloride (PVC) foams. Examples of acceptable woven fabric materials include: tricot fabrics; knit fabrics; and loose weave fabrics. Examples of acceptable non-woven fabric materials include: spunlace fabrics; microporous fabrics; and elastic fabrics. Examples of acceptable gel materials include: hydrogel adhesives; hydrocolloid adhesives; encapsulated gels. In those embodiments that include an optically transparent portion 94 and an optically non-transparent portion 96, the material(s) of those portions 94, 96 may be different from one another. A specific example of an acceptable optically transparent material is a polyethylene foam product with a pressure sensitive adhesive offered by Avery Dennison, Inc., product name Avery-Med 362.

The subject contact layer 34 aids in reducing or eliminating discomfort to the subject that components of the NIRS sensor assembly 10 might otherwise cause the subject. For example, in certain applications it is possible that the light source 22 may act as a heat source that, over time, can cause the subject to experience discomfort in the absence of the subject contact layer 34. In such applications, the subject contact layer 34 may act as a thermal barrier that decreases the amount of thermal energy reaching the subject's skin from the light source. As another example, in certain applications it is possible that components in the NIRS sensor assembly 10 (e.g., the light source 22, the light detectors 26, 28, etc.) may create pressure points that can cause the subject discomfort in the absence of the subject contact layer 34. In such applications, the subject contact layer 34 may act as a cushioning layer that decreases the magnitude of, or eliminates, such pressure points. The cushioning effect produced by the subject contact layer 34 may be particularly advantageous in those applications where the subject's skin is fragile (e.g., neonatal skin, elderly skin, etc.).

In some embodiments, one or more components of the NIRS sensor assembly 10 may be disposed between the light source 22 and the subject contact layer 34, or between the light detectors 24, 26 and the subject contact layer 34. Those components include EMI shielding 86 that may be in the form of a single section, or a plurality of discrete sections. In the embodiment shown in FIG. 6, for example, the layer of EMI shielding 86 includes three discrete sections: a first section 88 disposed relative to the light source 22, a second section 90 disposed relative to the light detector 24 that is closest to the light source 22, and a third section 92 disposed relative to the light detector 26 that is farthest from the light source 22. The EMI shielding 86 may be made of any acceptable material, or combination of materials, operable to shield against EMI. Examples of acceptable EMI shielding 86 materials are disclosed in U.S. Patent Application No. 61/735,318. In some embodiments, one or more layers of electrically insulating material (not shown) may additionally or alternatively be disposed between the light source 22 and the subject contact layer 34, or between the light detectors 24, 26 and the subject contact layer 34. The layer of electrically insulating material may be made of any acceptable material, or combination of materials, that is electrically non-conductive. Examples of acceptable electrically insulating materials are disclosed in U.S. Patent Application No. 61/735,318. In some embodiments, one or more layers of EMI shielding 86 and/or one or more layers of electrically insulating material may be incorporated into the subject contact layer 34. For example, the subject contact layer 34 may include a plurality of sublayers, and a layer of EMI shielding 86 may be disposed between the sublayers.

Referring to FIGS. 2-7, the cover 36 is disposed relative to the circuit 28. In the embodiments illustrated in FIGS. 2-7, the cover 36 is attached (e.g., using adhesives) to the surface of the circuit 28 that is opposite the light source 22 and the light detectors 24, 26. The cover 36 can have various geometries. In FIG. 2, the cover 36 has a geometry that generally matches the geometry of the pad 32. The cover 36 can be made from various materials or combinations of materials. The cover 36 may preferably consist of a soft pliable material that can be used in a patient environment. Examples of acceptable cover 36 materials include: Tyvek®, a product made by DuPont; Poron® cellular urethane foam; vinyl materials, plastic materials; and foam materials.

Figure 8:
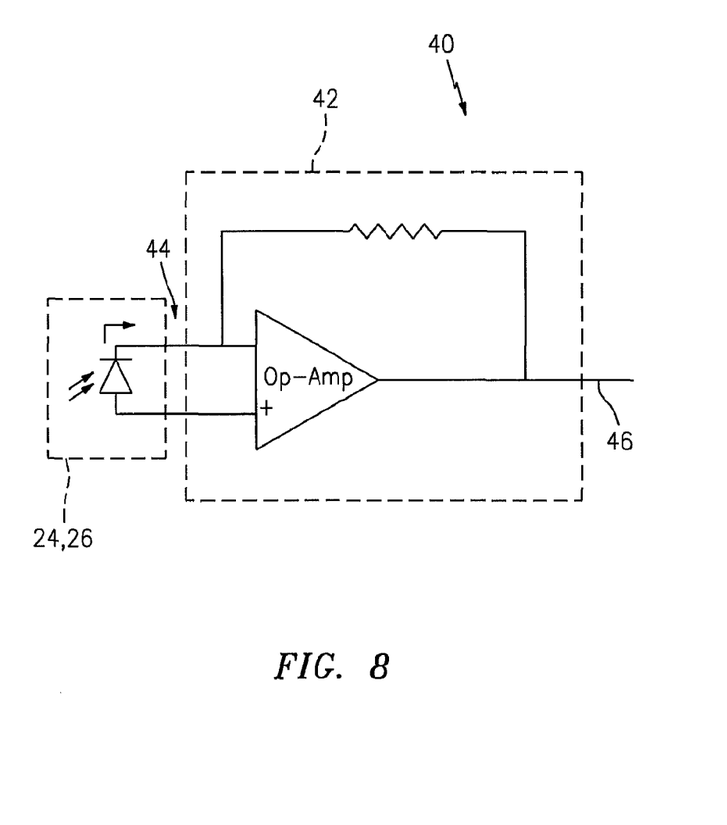
FIG. 8 is a circuit diagram showing a luminance measuring device.
Figure 9:
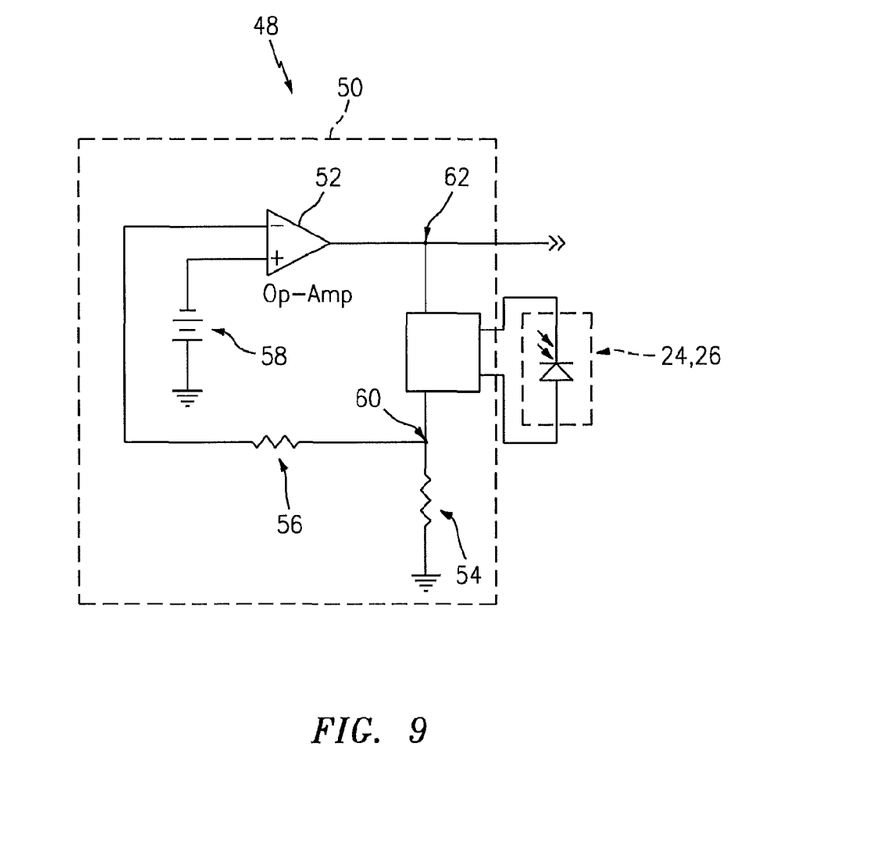
FIG. 9 is a circuit diagram showing a temperature measuring device.

The NIRS sensor assembly 10 may be configured so that one or more of the light detectors 24, 26 can be used in measuring the luminance and/or temperature of the light source 22. For example, in some embodiments, one or more of the light detectors 24, 26 may be positioned sufficiently close to the light source 22 so that the luminance of light signals detected by one or more of the light detectors 24, 26 is indicative of the luminance of the light emitted by the light source 22, and so that the temperature of one or more of the light detectors 24, 26 is indicative of the temperature of the light source 22. The NIRS sensor assembly 10 may include a luminance measuring device that is operable to measure the luminance of light detected by one or more of the light detectors 24, 26. Examples of acceptable luminance measuring devices are disclosed in U.S. patent application Ser. No. 13/543,180, which is hereby incorporated by reference in its entirety. FIG. 8 illustrates an example of a luminance measuring device 40 that is operable to measure the luminance of light detected by one of the light detectors 24, 26. The luminance measuring device 40 includes a photovoltaic circuit 42 that is zero biased and has a zero ohm input impedance. The input 44 of the photovoltaic circuit 42 receives signals from one of the light detectors 24, 26. The output 46 of the photovoltaic circuit 42 provides luminance signals relating to the luminance of the respective light detector 24, 26, which luminance signals may be transmitted to the base unit 14 (see FIG. 1) for processing. The processor 20 of the base unit 14 (see FIG. 1) may adjust a characteristic (e.g., luminance) of the light emitted by the light source 22 in response to the luminance signals. The NIRS sensor assembly 10 may include a temperature measuring device that is operable to measure the temperature of one or more of the light detectors 24, 26. Examples of acceptable temperature measuring devices are disclosed in U.S. patent application Ser. No. 13/543,180. FIG. 9 illustrates an example of a temperature measuring device 48 that is operable to measure the temperature of one of the light detectors 24, 26. The temperature measuring device 48 includes a circuit 50 for converting a signal received from one of the light detectors 24, 26 into a temperature signal indicative of the temperature of the respective light detector 24, 26. The temperature measuring device 48 includes a circuit 50 that biases one of the light detectors 24, 26 with a constant current. The circuit 50 includes an op-amp 52, a first load 54, a second load 56 and a voltage source 58. The input 60 of the circuit 50 receives a signal from one of the light detectors 24, 26. The output 62 of the circuit 50 provides temperature signals relating to the temperature of the respective light detector 24, 26, which signals may be transmitted to the base unit 14 (see FIG. 1) for processing. The processor 20 of the base unit 14 (see FIG. 1) may adjust a characteristic (e.g., luminance) of the light signals emitted by the light source 22 in response to the temperature signals.

During operation of the NIRS sensor assembly 10, the NIRS sensor assembly 10 is positioned relative to a biological tissue of a subject. Light signals emitted by the light source 22 pass through the subject contact layer 34, enter and exit the subject's tissue, pass back through the subject contact layer 34, and are thereafter detected by the light detectors 24, 26. Signals representative of the light signals detected by the light detectors 24, 26 are relayed back to the base unit 14, where they are processed by the processor 20 to obtain data relating to one or more characteristics (e.g., blood oxygenation) of the subject's biological tissue.

According to an aspect of the present invention, the processor 20 is adapted for use with a sensor assembly having a contact layer 34 as is described above; e.g., the processor 20 is adapted for use with sensor assemblies that include a subject contact layer 34, including one or more algorithms that include calibration accounting for light signals passing through the subject contact layer 34.

According to an aspect of the present invention, the processor 20 may be adapted for use with a "contact layer sensor assembly" using empirically collected data. For example, the blood oxygen saturation level of a clinically appropriate number of subjects may be sensed using a contact layer sensor assembly (as described herein), while at the same time (or a point close in time) empirical oxygen saturation data can be collected from the same subjects by discrete sampling or continuous monitoring. The temporal and physical proximity of the NIRS sensing and the development of the empirical data helps assure accuracy. Calibration parameters that may be necessary to create agreement between the empirically determined data values and the oximeter sensed data values may be determined using techniques similar to those described in U.S. Pat. No. 7,072,701, and the processor 20 adapted accordingly. In this way, the optical characteristics of the "contact layer sensor assembly" will be accounted for in the calibration parameters.

Alternatively, the processor 20 may be calibrated for use with a contact layer sensor assembly by sensing a phantom sample having known optical characteristics, preferably similar to that of biological tissue that would ordinarily be sensed by the NIRS system; e.g., skin, bone, brain, etc.) In this embodiment, the phantom sample may be sensed with one or more sensor assemblies without a contact layer 34, and one or more sensor assemblies with a contact layer 34. The difference in light signal attenuation could then be used to calibrate the processor 20 for subsequent use with a contact layer sensor assembly as is described herein.

While several embodiments have been disclosed, it will be apparent to those of ordinary skill in the art that aspects of the present invention include many more embodiments. Accordingly, aspects of the present invention are not to be restricted except in light of the attached claims and their equivalents.

What is claimed is:

1. A near-infrared spectroscopy (NIRS) system for measuring a characteristic of a biological tissue, comprising:
   at least one sensor assembly including a light source operable to emit light at one or more predetermined wavelengths, at least one light detector having an active area for detecting light emitted by the light source and passed through the biological tissue, and which detector is operable to produce signals representative of the detected light, and a subject contact layer disposed to cover at least one of the light source or the at least one light detector, which subject contact layer has an optically transmissive portion, the optically transmissive portion of the subject contact layer having at least one of known uniform optical attenuation characteristics or known uniform light scattering characteristics; and
   a processor adapted to use the signals produced by the detector to determine the characteristic of the tissue, and which processor is adapted to account for at least one of the known uniform optical attenuation characteristics or the known uniform light scattering characteristics in making such determination.

2. The NIRS system of claim 1, wherein the at least one sensor assembly further comprises a pad having at least one light detector aperture aligned with the light detector, and at least one light source aperture aligned with the at least one light detector; and
   wherein the subject contact layer is disposed to cover both the light source and the at least one detector, and wherein the at least one optically transmissive portion of the subject contact layer includes portions aligned with the light source and the at least one detector.

3. The NIRS system of claim 1, wherein the processor is adapted with empirically collected data that is representative of at least one of the known uniform optical attenuation characteristics or the known uniform light scattering characteristics.

4. A method for determining a blood oxygen parameter of a subject tissue, comprising the steps of:
   providing a near-infrared spectroscopy (NIRS) system, which system includes at least one sensor assembly and a processor, wherein the at least one sensor assembly includes:
      a light source operable to emit light at one or more predetermined wavelengths;
      at least one light detector having an active area for detecting light emitted by the light source and passed through the biological tissue, the detector configured to selectively produce signals representative of the detected light; and
      a subject contact layer having at least one optically transmissive portion, the optically transmissive portion having at least one of known uniform optical attenuation characteristics or known uniform light scattering characteristics, the at least one optically transmissive portion disposed to cover at least one of the light source or the at least one light detector;
   interrogating the subject tissue with light emitted from the sensor assembly;
   detecting light emitted by the light source, which light has passed through the biological tissue and has passed through the at least one optically transmissive portion, and producing signals representative of the detected light; and
   determining the blood oxygen parameter of the subject tissue using the processor, the signals representative of the detected light, and calibration stored within the processor that is representative of at least one of the known uniform optical attenuation characteristics or the known uniform light scattering characteristics.

5. The method of claim 4, wherein the stored calibration is based on empirically collected data that is representative of at least one of the known uniform optical attenuation characteristics or the known uniform light scattering characteristics.

6. The method of claim 4, wherein the sensor assembly further comprises a pad having at least one light detector aperture aligned with the light detector, and at least one light source aperture aligned with the at least one light detector; and
   wherein the subject contact layer is disposed to cover both the light source and the at least one detector, and wherein the at least one optically transmissive portion of the subject contact layer includes portions aligned with the light source and the at least one detector.

7. The NIRS system of claim 1, wherein the subject contact layer is made from one or more materials selected from the group consisting of: a silicone foam, a polyethylene foam, a polyurethane foam, or a polyvinyl chloride foam.

8. The NIRS system of claim 1, wherein the subject contact layer is made from one or more materials selected from the group consisting of: a tricot fabric; a knit fabric, a loose weave fabric, a spunlace fabric, a microporous fabric, or an elastic fabric.

9. The NIRS system of claim 1, wherein the subject contact layer is made from one or more materials selected from the group consisting of: a hydrogel adhesive, a hydrocolloid adhesive, or an encapsulated gel.

10. A near-infrared spectroscopy (NIRS) system for measuring a characteristic of a biological tissue, comprising:
- at least one sensor assembly including a light source operable to emit light at one or more predetermined wavelengths, at least one light detector having an active area for detecting light emitted by the light source and passed through the biological tissue, and which detector is operable to produce signals representative of the detected light, and a subject contact layer disposed to cover at least one of the light detector or the light source, which subject contact layer has an optically transmissive portion, the optically transmissive portion of the subject contact layer having at least one of known uniform optical attenuation characteristics or known uniform light scattering characteristics; and
- a processor in communication with the at least one sensor assembly and a non-transitory memory storing instructions, which instructions include calibration that accounts for at least one of the known uniform optical attenuation characteristics or the known uniform light scattering characteristics, and which instructions when executed cause the processor to determine the characteristic of the tissue using the calibration.

* * * * *